(12) United States Patent
Chalvignac (10) Patent No.: US 7,874,290 B2
(45) Date of Patent: Jan. 25, 2011

(54) BREATHING ASSISTANCE DEVICE (75) Inventor: Philippe Chalvignac, Achères la Forêt (FR)

(73) Assignee: ResMed Paris (FR)

( * ) Notice: Subject to any disclaimer, the term of this patent is extended or adjusted under 35 U.S.C. 154(b) by 901 days.

(21) Appl. No.: 10/563,493

(22) PCT Filed: Jul. 5, 2004

(86) PCT No.: PCT/IB2004/002440

§ 371 (c)(1),
(2), (4) Date: Jan. 4, 2006

(87) PCT Pub. No.: WO2005/002655

PCT Pub. Date: Jan. 13, 2005

(65) Prior Publication Data

US 2006/0150973 A1   Jul. 13, 2006

Related U.S. Application Data

(60) Provisional application No. 60/495,922, filed on Aug. 18, 2003.

(30) Foreign Application Priority Data

Jul. 4, 2003   (FR) .................................. 03 08187

(51) Int. Cl.
*A61M 16/00* (2006.01)
*A62B 7/00* (2006.01)

(52) U.S. Cl. ........................... 128/204.21; 128/200.24; 128/204.18

(58) Field of Classification Search ............ 128/204.21, 128/204.18, 204.19, 200.24, 201.22–201.24, 128/206.21, 206.23, 206.28

See application file for complete search history.

(56) References Cited

U.S. PATENT DOCUMENTS

| 3,649,964 | A | * | 3/1972 | Schoelz et al. | 128/205.25 |
|---|---|---|---|---|---|
| 4,590,951 | A | * | 5/1986 | O'Connor | 128/204.23 |
| 5,303,701 | A | * | 4/1994 | Heins et al. | 128/206.17 |
| 6,050,262 | A | * | 4/2000 | Jay | 128/205.27 |
| 6,257,235 | B1 | * | 7/2001 | Bowen | 128/206.21 |
| 6,382,208 | B2 | * | 5/2002 | Reedy et al. | 128/204.17 |
| 6,435,184 | B1 | * | 8/2002 | Ho | 128/206.21 |
| 6,467,477 | B1 | * | 10/2002 | Frank et al. | 128/203.23 |
| 6,581,595 | B1 | * | 6/2003 | Murdock et al. | 128/204.18 |
| 6,854,464 | B2 | * | 2/2005 | Mukaiyama et al. | 128/206.17 |
| 2002/0185130 | A1 | * | 12/2002 | Wright et al. | 128/204.21 |
| 2003/0066527 | A1 | * | 4/2003 | Chen | 128/204.18 |

(Continued)

FOREIGN PATENT DOCUMENTS

DE   101 16 361 A1   10/2002

(Continued)

*Primary Examiner*—Quang D Thanh
(74) *Attorney, Agent, or Firm*—Lerner, David, Littenberg, Krumholz & Mentlik, LLP (57) ABSTRACT

A breathing assistance device (10) for a patient, comprising: A source of respiratory pressurised gas (105), A breathing connection (120) to allow the patient to receive said gas, At least one sensor for acquiring a parameter representative of the operation of the device (10), wherein said gas source (105) is a ventilator (210), and said ventilator (210) is integrated into a removable module (20) which also comprises at least one sensor for acquiring a parameter representative of the operation of the device (10).

17 Claims, 3 Drawing Sheets

U.S. PATENT DOCUMENTS

2003/0172930 A1 * 9/2003 Kullik et al. ........... 128/204.18

FOREIGN PATENT DOCUMENTS

| EP | 0 164 946 A | 12/1985 |
| FR | 2 784 587 A | 4/2000 |
| FR | 2 837 108 A | 9/2003 |
| WO | WO-03/049793 A2 | 6/2003 |

* cited by examiner

BREATHING ASSISTANCE DEVICE

CROSS REFERENCE TO RELATED APPLICATIONS

The present application is a U.S. national stage application of International Application No. PCT/IB2004/002440, filed on Jul. 5, 2004, which claims the benefit of French Application No. 0308187, filed on Jul. 4, 2003, and of U.S. Provisional Patent Application No. 60/495,922, filed on Aug. 18, 2003, each of which is incorporated herein by reference in its entirety.

BACKGROUND OF THE INVENTION

The present invention generally relates to breathing assistance devices.

More precisely, the invention concerns a breathing assistance device for a patient, comprising:
  A source of respiratory pressurised gas,
  A breathing connection to allow the patient to receive said gas,
  At least one sensor for acquiring a parameter representative of the operation of the device.

Devices of this type are already known.

Figure 1:
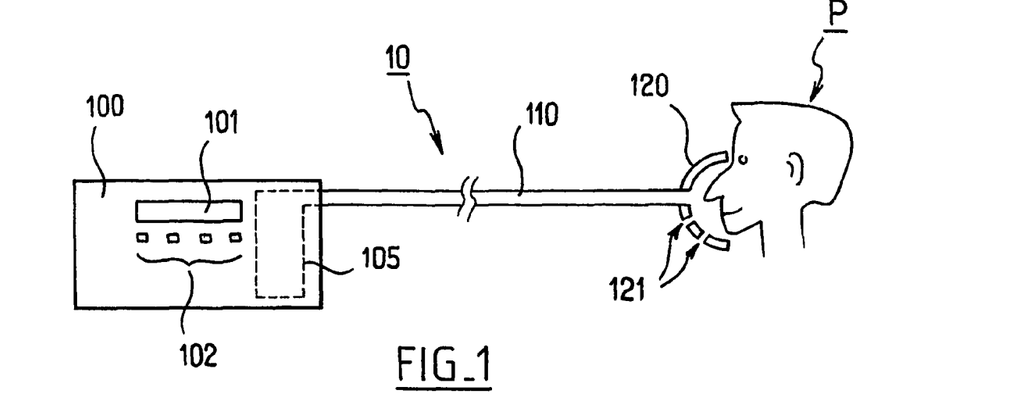

FIG. 1 therefore diagrammatically illustrates an example 10 of a known device.

The device 10 comprises a fixed console 100.

This fixed console 100 comprises among others a source of pressurised gas 105.

In practice, this gas source can be in the form of a ventilator or a fan (the term ventilator is retained in the text hereinbelow for convenience).

The ventilator is mounted fixed inside the console.

The fixed console 100 also generally comprises a central unit for controlling the operation of the device.

Such a central unit is connected to one or more sensors of parameter(s) representative of the operation of the device (typically the gas flow rate and the gas pressure), and it controls the operation of the device as a function of this/these parameter(s).

The console comprises means for interfacing with a user (who can be the patient himself).

These means are illustrated schematically here in the form of a screen 101 and control/adjustment buttons 102.

The respiratory gas is conveyed from the source 105 to the patient via a conduit 110, whereof a first end is connected to said source.

The second end of the conduit 110 will be generally designated in this text by the term "breathing connection".

More generally still, a <<breathing connection >> designates in this text the interface between the device and the patent.

Such a <<breathing connection >> can correspond to a breathing mask, as illustrated in the illustration in FIG. 1.

It is specified that it is also envisageable to utilise a device of this type in so-called « intrusive » mode, where the patient is then intubated with this second end.

In this latter case, the <<breathing connection >> corresponds simply to the end of the conduit with which the patient is intubated.

In the example illustrated in FIG. 1, the mask 120 comprises vents 121 for arranging leaks of respiratory gas. These leaks especially allow a part of the CO2 rejected by the patient to be evacuated during expiration phases.

The elements described hereinabove in reference to FIG. 1 are found in a large number of known devices.

These devices provide substantial assistance.

They are nonetheless associated with certain disadvantages, and certain limitations. Certain of these disadvantages/limitations will be explained hereinbelow.

First of all, the general configuration of such devices generally leads to fairly significant space requirements (due to the presence of the fixed console, the conduit connecting the console and the patient, possibly other conduits such as an expiration conduit.).

This space requirement can constitute a disadvantage per se.

In addition, this general configuration also gives rise to constraints for the patient.

In particular, the patient must remain attached to the fixed console, by way of the conduit.

This naturally limits the movements of the patient, and can constitute an inconvenience (especially at night, within the scope for example of sleep apnoea treatment).

Furthermore, in such a general configuration, even if a certain proportion of the CO2 expirated by the patient can escape via the vents of the mask, the remaining proportion of CO2 is <<trapped >> in the conduit, where it is forced back during expiration.

A <<plug >> of CO2 is thus formed in the conduit. And pollutants such as for example germs expirated by the patient can be found in this <<plug >>.

This plug of CO2 can thus constitute pollution for the patient, who can possibly be induced to inspire a part of the CO2 and germs expirated previously.

This plug of CO2 can also constitute pollution for the device, where it is capable of migrating or being pushed towards elements of the device such as the gas source located at the end of the conduit 110.

The presence of CO2 and its possible pollutants in such elements of the device can even constitute a danger for the patient.

In fact, in the case where CO2 and/or pollutants would be present in such elements of the device, the device would risk conveying this CO2 and/or these pollutants to the patient.

This can constitute a danger for the patient (especially in the case of hypercapnic patients).

It is thus necessary in this case to proceed with disassembling and cleaning these elements. This constitutes a fastidious operation, which also makes the device unavailable.

It will also be noted that even by abstracting the specific problem of pollution which has just been explained à propos CO2 trapped in a conduit, patients are exposed to the disadvantages associated with cleaning operations mentioned hereinabove.

Therefore, the known devices are exposed to these disadvantages, which are considered particular causes of pollution (associated or not with the conduit), or not.

It is thus necessary from time to time to proceed with disassembling and cleaning the ventilator, which, as explained, constitutes a fastidious operation, and which also has the disadvantage of making the device unavailable.

With respect to the aspects associated specifically with the general configuration comprising a console and a conduit, it is also to be noted that the presence of the conduit causes losses of charge and pneumatic inertia:
  which diminish the energetic yield of the device,
  and which increase the complexity of the control of the device, where these losses of charge and inertia must be integrated into the control programs of the device.

This disadvantage is naturally all the more sensitive than the conduit is long.

Furthermore, limitations and disadvantages are associated specifically with the presence of the mask vents.

And in certain applications (especially in the case of a device functioning in BPAP or CPAP mode), the known devices generally utilised take on the configuration illustrated FIG. 1, which comprises a mask with vents.

It is specified that the CPAP type (acronym of the English term Continuous Positive Airway Pressure—this type also able to be designated in French by the acronym PPC for Pression Positive Continue [Continuous Positive Pressure]) designates the devices at a single pressure level.

In these devices, the speed of rotation of the ventilator is regulated by measuring the pressure exerted on the single conduit of the device (conduit 110 in FIG. 1).

The unique control pressure is generally fixed at a value less than 20 mbars (this value is expressed in surpressure relative to atmospheric pressure), which limits the use of such devices to the treatment of light pathologies.

The devices of BPAP type (acronym of the English term Bilevel Positive Airway Pressure, this acronym being a registered trade mark—and this type also able to be designated in French by the acronym VNDP for Ventilation Nasale à Deux niveaux de Pression [Nasal Ventilation at two Pressure Levels]) has the same general architecture, but functions with two control pressures (a value of inspiration pressure and a value of expiration pressure).

The devices mentioned hereinabove referring to FIG. 1 (in particular operating in BPAP or CPAP mode) therefore often comprise masks with vents.

Such a mask with vents can cause unwanted effects.

In particular, the gas outlets associated to the vents can be directed towards parts of the body of the patient, and cause phenomena such as desiccation of these parts of the body.

This is a disadvantage, especially when such consequences are observed in the eyes of the patient.

In addition, leaks must be taken into consideration for administering the operation of the device (for example consideration of these leaks in the programs of the central unit which administers this operation).

This naturally tends to increase the complexity of the device.

It thus appears that certain disadvantages and limitations are linked to the known devices described hereinabove.

The aim of the invention is to eliminate these disadvantages.

SUMMARY OF THE INVENTION

In order to attain this goal, the invention proposes a breathing assistance device for a patient, comprising:

A source of respiratory pressurised gas,

A breathing connection to allow the patient to receive said gas,

At least one sensor for acquiring a parameter representative of the operation of the device, characterised in that said gas source is a ventilator, and said ventilator is integrated into a removable module which also comprises at least one sensor for acquiring a parameter representative of the operation of the device.

Preferred but non-limiting aspects of such a device are the following:

said module comprises a respiratory gas pressure sensor and a flow sensor, the module is fixed on the device by a removable connection, such that disassembly of the module is made easier, said removable connection comprises a thread pitch, said removable connection comprises means for clipping the module, said breathing connection is made in the form of a mask, said mask is a mask without means enabling leaks, such as vents, the module is fixed directly on the breathing connection, such that the device does not comprise a conduit for conveying respiratory gas which would connect the breathing connection to a fixed offline console of the device, the ensemble formed by the breathing connection and the module is linked to a control console of the device, said link permits transmission between said ensemble and said data console, said link is a wireless link, said link enables the energy required for operating the components of the module to be conveyed from said console to said ensemble, said link is a wire link, the ventilator is an axial ventilator, the rotor of the ventilator axial comprises a single stage, in the ventilator the respective directions of the input and the output of respiratory gas are substantially parallel, the ventilator comprises:
  a central input substantially aligned with the axis of rotation of the rotor of the ventilator,
  an outlet allowing the flux generated by said rotor to be collected according to an oblique direction relative to said axis of rotation, and
  means for rectifying said flux generated and collected, so that this flux flows out of the ventilator in a general direction substantially parallel to said axis of rotation of the rotor of the ventilator, the device is of type BPAP, the device is of type CPAP.

A number of devices or systems have been proposed for assisting patients to breathe—as an example one can refer to FR 2 784 587, WO 03/049793 and DE 101 16 361—but such devices do not disclose or even suggest the specific features of the invention (to begin with a ventilator arranged into a removable module).

BRIEF DESCRIPTION OF THE DRAWINGS

Other aspects, aims and advantages will emerge better from reading the following description of the invention, made in reference to the attached diagrams in which, apart from FIG. 1 on which comment has already been made in reference to the prior art.

DETAILED DESCRIPTION

Figure 2:
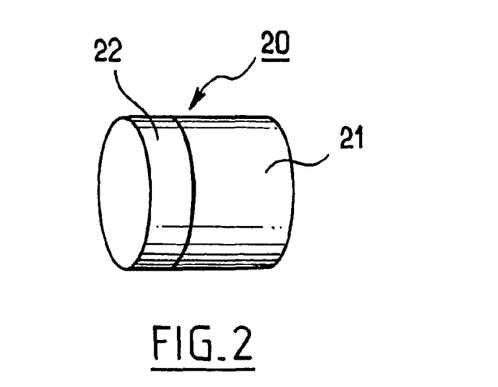
FIG. 2 is a diagrammatic illustration of a module put to use in a device according to the present invention.

FIG. 2 diagrammatically illustrates a module 20.

This module has the general form of a cylinder with a circular base.

The diameter of this cylinder can for example be of the order of 25 to 35 mm.

The module 20 comprises two main parts:

A first part 21, which contains a ventilator,

A second part 22, which contains one or more sensors for acquiring parameter(s) representative of the operation of the ventilator and of the flux of respiratory gas generated by this ventilator.

The module 20 is fitted with removable fixing means, for cooperating with complementary means of the device.

The module 20 is in effect intended to be able to be mounted and dismounted in a removable and simple manner on the device according to the present invention.

And, as will be seen, this module 20 can be implanted into different places in the device, according to embodiments of the invention.

The part 21 thus contains a ventilator, which is capable of generating a flux of respiratory pressurised gas.

To increase the compactness of the module 20, and permit dimensions of the order of those mentioned hereinabove (25 to 35 mm in diameter), the ventilator must have a specific configuration.

More precisely, this ventilator is an axial ventilator (which signifies that the air exits this ventilator in a direction substantially parallel to the axis of rotation of the revolving elements of the ventilator).

The applicant has in fact determined that this type of ventilator had less space requirement than a ventilator of centrifugal ventilator type, in which the gas exits in a direction tangential to the rotation disk of the rotor of the ventilator.

In particular, the embodiment of such a ventilator would require providing around the rotor a collection and rectification channel of the flux which would substantially increase the diameter of the module.

Figure 3A:
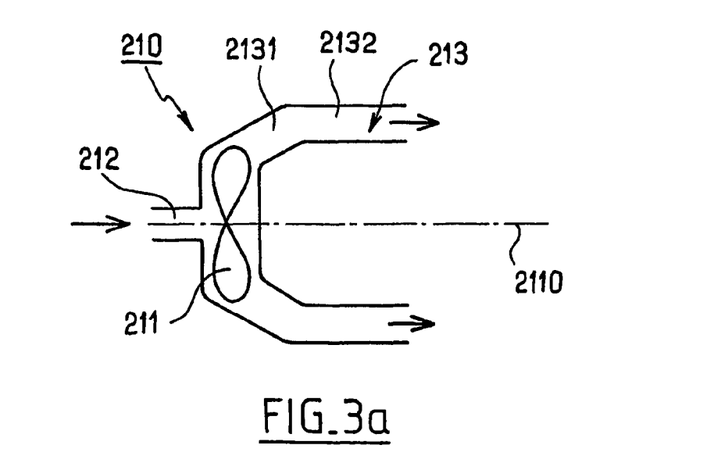
FIG. 3a is a diagrammatic illustration of a ventilator which can be used in a module according to the present invention, this ventilator being illustrated according to a longitudinal section.

FIG. 3a thus diagrammatically illustrates an embodiment of the axial ventilator contained in the part 21 of the module.

This figure diagrammatically illustrates a ventilator 210, provided with a rotor 211 capable of revolving about an axis of rotation 2110.

The rotor is driven by a motor integrated into the ventilator (motor not shown for the sake of clarity).

It is specified that the rotor can be a single-stage rotor (that is, comprising only a single series of blades), or a two-stage rotor (that is, comprising two series of blades mounted behind the other on the axis of rotation).

An air inlet 212 is provided, opposite the centre of the rotor 211. This air inlet is axial (it introduces the air aspirated by rotation of the rotor in a direction parallel to that of the axis of rotation 2110).

The air is expelled from the ventilator via an outlet 213 (which is here shown in section in the form of two conduits, and which can have a geometry of revolution around the axis of rotation 2110).

It will be noted that the section of the outlet 213 comprises two main parts:

A first part 2131 which is immediately adjacent to the rotor. This part 2131 is oriented obliquely relative to the axis 2110, so as to collect with maximum efficiency the flux of gas pushed by the rotor—the speed of this flux not only has an axial component (parallel to the axis 2110), but also a tangential component, A second part 2132, which is downstream of the first part 2131 and which is oriented substantially parallel to the axis 2110, such as to rectify the flux originating from the ventilator in the axial direction of this ventilator.

Arranging the two parts 2131 and 2132 is done such as to minimise the space requirement of the ventilator, and especially so as to conserve a reduced diameter for this ventilator.

The second part 22 of the module 20 comprises at least one sensor for acquiring a parameter representative of the operation of the device.

More precisely, in a preferred embodiment of the invention this part 22 comprises at least one pressure sensor and one flow sensor.

Figure 3B:
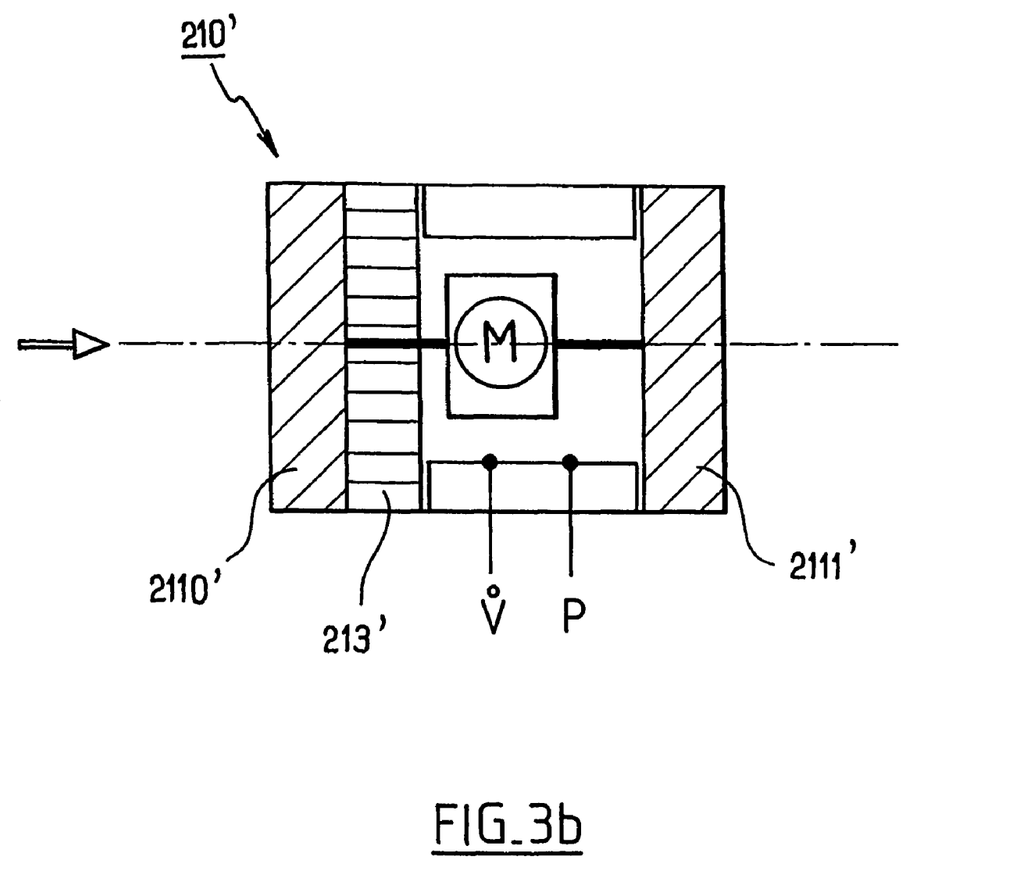
FIG. 3b is a diagrammatic illustration of another ventilator which can be used in a module according to the present invention, this ventilator being illustrated according to a longitudinal section.

FIG. 3b represents another possible configuration for an axial ventilator 210' contained in the part 21 of the module.

This ventilator comprises an inlet rotor 2110', moved in rotation by a motor M.

The motor M can also move in rotation another rotor 2111', located at the outlet of the ventilator.

Redressing means 213' can be provided immediately downstream of the inlet rotor.

At least one sensor for acquiring a parameter representative of the operation of the device is located in the part of the ventilator which is downstream of the inlet rotor (and of the redressing means if there are any).

More precisely, in a preferred embodiment of the invention this part comprises at least one pressure sensor and one flow sensor.

The module 22 also comprises means for amplifying and digitalising signals originating from the sensors of the part 22 (or of the part 21 if the sensors are located into this part), and a means of exchanging these signals with an offline console of the device.

This offline console can be a fixed console as in the prior art.

This console can also be a removable console, in the form of a device of reduced size.

Figure 4A:
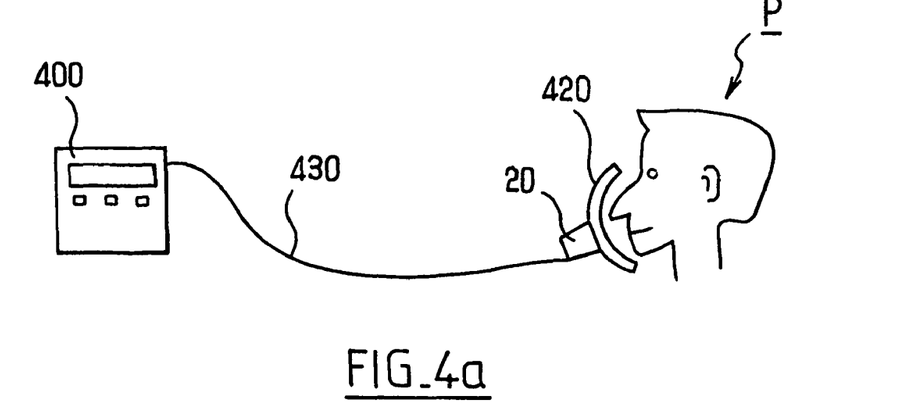
FIGS. 4a and 4b are a diagrammatic illustration of two variants of utilising the invention.

FIG. 4a illustrates a first variant embodiment of the invention.

In this figure, a patient P is shown breathing via a mask 420.

This mask 420 corresponds to the <<breathing connection>> which has been mentioned in the introduction to this text, and which allows the patient to breathe the gas coming from a source of pressurised gas.

In the different variant embodiments of the invention, it is in fact generally preferred to have the breathing connection made in the form of a mask (and as will be seen more precisely, a mask without vents).

Nevertheless it is specified that all the variant embodiments of the invention which are put forward in this text can be realised with a breathing connection which does not correspond to a mask, but to an end of a conduit or a portion of conduit allowing the patient to be intubated.

With respect to FIG. 4a, it is noticed that the mask 420 is not provided with any opening allowing leaks, such as vents.

The mask 420 is thus adapted to allow practically no gas leak.

And it should be further noticed that the breathing connection is not associated to any expiratory valve (also sometimes referred to as "exhalation valve").

This configuration without leakage means such as vents in a mask or an expiration valve allows:

To make the design, the construction and the operation of the device simple,

To maximally benefit from the proximal effect associated with a ventilator arranged in the vicinity of the mask, which prevents the formation of a $CO_2$ plug.

In this respect, the invention is totally different from devices such as the one disclosed by EP 164 946:

- It should first be noted that the device of EP 164 946 belongs to quite a different category of devices—it is a device which is merely designed for filtering the air inspired by a user and there is no arrangement for ventilating a patient according to different modes (in particular it is of course not possible in the case of the device of EP 164 946 to control the operation selectively in a barometric mode, or in a volumetric mode),
- This difference with the very nature of the device of EP 164 946 is further illustrated by the fact that the compressor of this device is considered as an element that is not even worth cleaning—rather, it is merely replaced when necessary,
- The device of EP 164 946 is arranged with an expiratory valve 8—which is perfectly understandable since in this filtering device it is desired to avoid breathing out through the filter. In this respect the present invention provides a device for which it is possible to breathe out directly through the turbine (in the versions of the invention where the turbine is in the direct vicinity of the mask so that there is no inspiration duct).

A module 20 of the type described in reference to FIG. 2 is connected to the mask 420.

More precisely, the module 20 is fixed in a removable manner on the mask by removable fastening means such as for example means comprising a thread pitch, or clipping means.

It is specified that generally any removable fastening means can be adopted to ensure fixing of the module onto the mask 420 (and more generally onto any part of the device intended to receive the module).

The module 20 is fixed onto the mask 420 such that the ventilator of this module feeds the internal space of the mask with respiratory gas.

FIG. 4a also illustrates an offline console 400.

This console comprises interface means such as a screen and control buttons, as the console 100 of FIG. 1.

It will be noted all the same that in the case of the device in FIG. 4a, no ventilator or source of pressurised gas is connected to the console.

In effect, in this case the ventilator is directly connected to the mask 420.

The console 400 may integrate a central control unit for operating the device.

In this case, this control unit receives the signals originating from the sensors of the module 20.

To this end, the signals have previously been amplified and digitalised in the module, by the means mentioned hereinabove.

Transmission of signals between the module 20 and the central unit of the console 400 is made in the case of the device of FIG. 4a by a link of wire type.

In this case, a data transmission cable 430 assures transmission of the signals from the module to the central unit.

As a function of the value of these signals, the central unit works out a control value of the speed of rotation destined for the ventilator.

This control value can in particular be a value of the speed of rotation of the rotor of the ventilator.

This order is transmitted to the ventilator via the same link between the console and the module (in the case of the device in FIG. 4a, the cable 430).

It is understood that the device in FIG. 4a offers numerous advantages.

In particular, it is noted that no conduit connect the console 400 and the patient to draw off the respiratory gas to said patient.

This offers considerable comfort and extensive flexibility in use.

In addition, the absence of conduit effectively eliminates the disadvantages mentioned in the introduction to this text with reference to plugs of CO2 which can be created in the conduits of the known devices.

This is an important advantage, which can be referred to as the "proximal effect".

And more generally (and abstracting the considerations associated with the presence or not of a conduit), the fact that the module is removable allows the ventilator to be disassembled rapidly and simply, in order to proceed with cleaning it, if required.

Furthermore, since the mask is provided without vents, in the case of the invention there is no exposure to the disadvantages associated with the presence of such vents.

It will also be noted that the fact that the ventilator and its associated sensors are placed closer to the patient allows parameters which are actually representative of the state of the gas in the vicinity of the patient to be transmitted to the central unit controlling the operation of the device.

It is specified in this regard that implantation of the module in the mask is done so as to let only a small volume inside the mask.

Operation of the device can thus be tracked by the central unit in <<truly >> real time, with a response time which is extremely low relative to the status changes of the device.

In particular, the fact of being free of the length of the conduit conventionally conveying the gas to the patient allows the operation of the device to be tracked closely: the effect of the commands transmitted to the ventilator will have immediate repercussions on the patient.

Another advantage holds that the motor of the ventilator is in the immediate vicinity of the sensors of the part 22 of the module 20.

The heat released by this motor in effect reheats the respiratory gas passing into these sensors, which effectively prevents the condensation of gas near these sensors.

It will be noted that the patient can use a remote control to control the operation of the console 400 from a distance.

Furthermore, the console 400 can itself be reduced to a simple remote control allowing the operation of the device to be controlled.

Figure 4B:
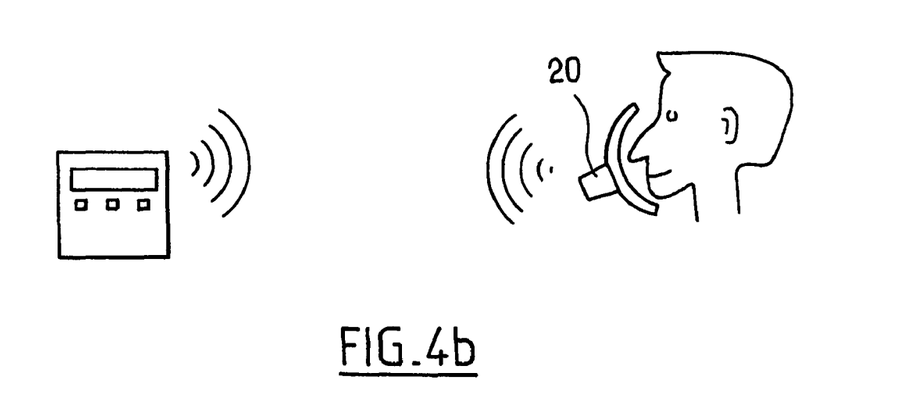

FIG. 4b illustrates another variant embodiment of the invention.

In this variant, the link between the offline console 400 and the module 20 is made by a wireless link.

This wireless link of the device in FIG. 4b effectively transfers data and signals mentioned hereinabove, by means of wireless transmission.

Such means can for example comprise a radiofrequency transmitter and receiver. This can for example be a link of BlueTooth type (registered trade mark).

In the case of the variant illustrated in FIG. 4b, the ventilator of the module 20 is associated with a small electric battery which is also integrated into the module.

The other characteristics of the device of FIG. 4b are similar to those of the device of FIG. 4a.

Figure 5:
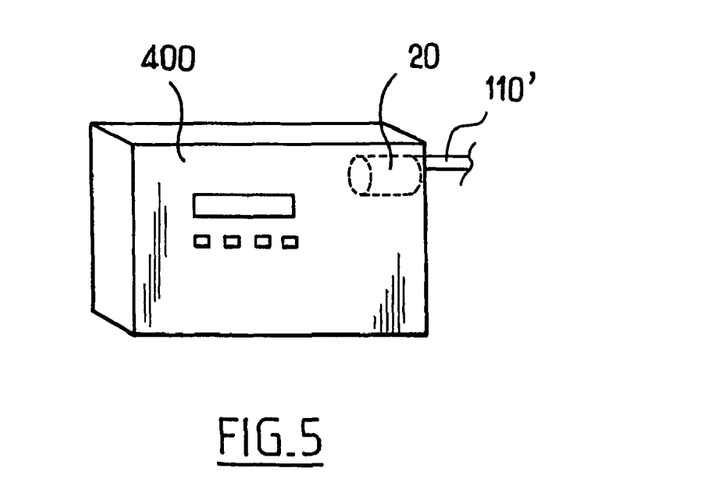
FIG. 5 is a diagrammatic illustration of a console which can be utilised in another variant of the invention.

FIG. 5 illustrates another mode of realisation of the invention, which corresponds to an alternative embodiment.

In this alternative, the module 20 is not fixed directly on the mask 420 of the patient. Instead of this, the module 20 is mounted on the console 400, or in this console.

In this case, a conduit 110' still connects the console to the mask of the patient, to bring it the respiratory gas which it needs.

This alternative embodiment does not offer all the advantages mentioned hereinabove with reference to the devices of FIGS. 4*a* and 4*b*, in which the module 20 is directly implanted onto the mask of the patient.

But the alternative of FIG. 5 all the same allows simple, rapid and easy disassembly of the ventilator, for cleaning purposes, for example.

And in this case also, the ventilator is an axial ventilator, of the type illustrated in FIG. 3*a*.

It is specified that this type of axial ventilator, apart from the fact that it effectively reduces the space requirement associated with the module 20, also offers an advantage in terms of operation.

In this respect, it is firstly recalled that breathing assistance devices can be tracked under flow, or pressure.

In flow tracking, the operation of the ventilator is controlled essentially as a function of the signals coming from a flow sensor of the respiratory gas.

This type of tracking corresponds to a so-called volumetric mode of the device.

It is also possible to track the device in barometric mode.

In this case, the control signals destined for the ventilator are worked out essentially as a function of the signals coming from the pressure sensor of the respiratory gas.

Such barometric tracking is often adopted to ventilate patients afflicted with light pathologies (especially patients suffering from sleep apnoea).

And the applicant has ascertained that a ventilator of axial type was more capable than a ventilator of centrifugal type in keeping track of the device under pressure.

In effect, such an axial ventilator is particularly well adapted to generate a flux of respiratory gas with:

relatively low pressures (whereof the value is less than around 25 mb), with an increased rate (typically having a value greater than around 150 l/min).

And this type of pressure and flow values is currently associated with modes of operation in BPAP or in CPAP, which correspond to operating modes of the invention.

It is also specified that using an axial ventilator as a source of pressurised gas can help boost the safety of the device.

In effect, in the case of a power cut depriving the source of pressurised gas of electrical power, it will be much easier for the patient to continue to breathe <<through >> an axial ventilator than <<through >> any other type of source of pressurised gas.

Another advantage still of a source of pressurised gas in the form of an axial ventilator is that the noise associated with operating such a source is diminished. The comfort of use of the device is increased—especially within the scope of treating sleep apnoea. In all the cases in point, the device according to the present invention can be a device of type BPAP or CPAP.

The invention claimed is:

1. A breathing assistance device for a patient, comprising:
   a source of respiratory pressurized gas, where the gas source is a ventilator having an inlet rotor and a motor;
   a breathing connection for allowing the patient to receive said pressurized gas;
   at least one sensor for acquiring a parameter representative of the operation of the device;
   a central control unit for operating the device in at least one airway pressure ventilation mode based on information from said at least one sensor; and
   a removable module removably connectable to the breathing connection, said removable module comprising a first part and a second part, wherein
   said ventilator is integrated into the first part of the removable module,
   said at least one sensor is contained in the second part of the removable module at a position downstream of the first part of the removable module and in the vicinity of the motor of the ventilator in order to substantially prevent condensation of gas nearby said at least one sensor,
   the breathing connection is a mask such that the removable module is directly connectable to the mask.

2. The device of claim 1, wherein said removable module comprises a pressure sensor of respiratory gas and a flow sensor.

3. The device of claim 1, wherein said removable module is fixable on the device by a removable connection such that disassembly of the module is easy.

4. The device of claim 1, wherein said removable module is fixable in a removable manner on the mask by removable fastening means.

5. The device of claim 1, wherein said mask is a non-vented mask.

6. The device of claim 1, wherein an ensemble formed by the breathing connection and the removable module is linked with a link to a control console of the device integrating the central control unit.

7. The device of claim 6, wherein said link allows data to be transmitted between said ensemble and said central control unit.

8. The device of claim 7, wherein said link helps to convey energy required to operate components of the removable module from said console to said ensemble.

9. The device of claim 7, wherein said link is a wired link.

10. The device of claim 1, wherein the ventilator is an axial ventilator.

11. The device of claim 10, wherein the rotor of the axial ventilator comprises a single stage.

12. The device of claim 11, wherein in the ventilator the respective directions of the input and output of respiratory gas are substantially parallel.

13. The device of claim 10, wherein the ventilator comprises:
    a central input substantially aligned with an axis of rotation of the rotor of the ventilator,
    an outlet allowing flux generated by said rotor to be collected according to an oblique direction relative to said axis of rotation, and
    means for rectifying said flux that is generated and collected, so that the generated and collected flux flows out of the ventilator in a general direction substantially parallel to said axis of rotation of the rotor of the ventilator.

14. The device of claim 1, wherein the airway pressure ventilation mode is a BPAP mode.

15. The device of claim 1, wherein the airway pressure ventilation mode is a CPAP mode.

16. The device of claim 7, wherein said link is a wireless link.

17. A breathing assistance device for a patient, comprising:
    a source of respiratory pressurized gas, where the gas source is a ventilator having at least an inlet rotor and a motor;
    a breathing connection for allowing the patient to receive said pressurized gas;
    at least one sensor for acquiring a parameter representative of the operation of the device; and a central control unit for operating the device in at least one airway pressure ventilation mode based on information from said at least one sensor, wherein said ventilator is integrated into a removable module removably connectable to the breathing connection, wherein the breathing connection is a mask such that the removable module is directly connectable to the mask, and wherein said at least one sensor for acquiring a parameter representative of the operation of the device is located in the removable module at a position downstream of the inlet rotor of the ventilator and in the vicinity of the motor of the ventilator in order to substantially prevent condensation of gas nearby said at least one sensor.

* * * * *